United States Patent [19]

Batist et al.

[11] Patent Number: 4,917,827

[45] Date of Patent: Apr. 17, 1990

[54] PROCESS FOR THE PREPARATION OF 9(11)-DEHYDRO STEROIDS

[75] Inventors: Jacobus N. M. Batist, Kwintsheul; Nicolaas C. M. E. Barendse, Den Hoorn; Arthur F. Marx, Delft, all of Netherlands

[73] Assignee: Gist-Brocades N.V., Delft, Netherlands

[21] Appl. No.: 204,720

[22] Filed: Jun. 10, 1988

[30] Foreign Application Priority Data

Jun. 12, 1987 [NL] Netherlands .................. 87201122

[51] Int. Cl.$^4$ ................................................ C07J 1/00
[52] U.S. Cl. ................................... 552/602; 552/610; 552/640
[58] Field of Search ............ 260/397.3, 397.4, 397.45, 260/397.47, 397.5

[56] References Cited

U.S. PATENT DOCUMENTS

| | | | |
|---|---|---|---|
| 3,026,337 | 3/1962 | Barton et al. | 260/397.47 |
| 4,102,907 | 7/1978 | Shepard | 260/397.3 |
| 4,255,344 | 3/1981 | Imada et al. | 260/397.1 |

FOREIGN PATENT DOCUMENTS

| | | |
|---|---|---|
| 2814747 | 4/1978 | Fed. Rep. of Germany . |
| 2387245 | 10/1978 | France . |
| 20528 | 12/1960 | German Democratic Rep. . |
| 7802302 | 3/1978 | Netherlands . |

OTHER PUBLICATIONS

Batist et al., CA 109:129460y (1988).
Gist—Brocades, CA 109:129454z (1988).
Paryzek et al., CA 94:139982f (1981).
Wydra et al., CA 104:6045f (1986).
ApSimon et al., CA 94:13038j (1981).
Bergstrom et al., "Acid—Catalysed Rearrangement of 9—alpha—hydroxy—4—androstene—3,17—dione", Chemistry and Industry, 9/1961, pp. 1530-1531.
Carlson et al., "Lewis Acids in Organic Synthesis . . . ", Acta Chemica Scandinavica, 1986, pp. 522-533.
Fadel et al., "Anhydrous Ferric Chloride Adsorbed on Silica Gel . . . ", Tetrahedron, vol. 41, No. 2, 1985, pp. 413-420.

*Primary Examiner*—Joseph A. Lipovsky
*Attorney, Agent, or Firm*—Fleit, Jacobson, Cohn, Price, Holman & Stern

[57] ABSTRACT

9(11)-dehydroandrostanes and 9(11)-dehydropregnanes are prepared by dehydrating the corresponding 9-alpha-hydroxy steroid in the presence of a Lewis acid. The corresponding 8(9)-dehydro-isomer was not detectable. The resulting products are valuable intermediates in steroid synthesis especially in the preparation of corticosteroids.

5 Claims, No Drawings

PROCESS FOR THE PREPARATION OF 9(11)-DEHYDRO STEROIDS

This invention relates to the preparation of 9(11)-dehydro steroids from the corresponding 9-alpha-hydroxy-compounds by dehydration.

Among the 9(11)-dehydro steroids the 9(11)-dehydroandrostanes and 9(11)-dehydropregnanes constitute an important group of intermediates in the synthesis of steroid drugs. They can be easily transformed into steroids with a 9-halogen-and/or an 11-hydroxy substituent, which substituents are characteristic of a large number of compounds belonging to the group of corticosteroids.

Various processes for the preparation of 9(11)-dehydrosteroids are already known, e.g. using dehydration of the corresponding 9-alpha-hydroxy compounds.

U.S. Pat. No. 3,065,146 describes dehydration using thionyl chloride in pyridine for the preparation of 9(11)-dehydroprogesterone. This method is also used for the dehydration of 9-alpha-hydroxyandrost-4-ene-3,17-dione.

Dutch patent application NL No. 7802302 indicates that using the procedure mentioned above a considerable amount of the 8(9)-dehydro isomer is produced as well. This causes a lower yield of the desired compound and a further disadvantage is that the removal of the undesired isomer is very complicated and costly.

DDR patent DL No. 20528 provides an easy method of preparation of 9(11)-dehydrosteroids, which comprises boiling a solution of the corresponding 9-alpha-hydroxy compound with an aromatic sulphonic acid, especially p-toluenesulphonic acid. Although the use of 9-alpha-hydroxy-testosterone is specifically mentioned, the examples only refer to pregnanes. The patent specification contains few and vague data about yield and purity. The method fails when applied to 9-alpha-hydroxyandrostanes. No 9(11)-dehydroandrostane is formed at all, as confirmed by C. G. Bergstrom and R. B. Dodson (Chemistry and Industry, 1530 (1961)).

An improved process is described in German patent application DE No. 2806687. The 9-alpha-hydroxyl group of an androstane compound is converted first into a 9-alpha-OSOR-group (R is (1-4C)alkyl, phenyl or substituted phenyl) by reaction with a sulfinyl chloride. By boiling the product subsequently in benzene with silica gel or alumina and an acid, a desulfination reaction takes place, giving the desired 9(11)-dehydrocompound in yields of not less than 85% and with a ratio 9(11)-dehydro: 8(9)-dehydro isomers being not lower than 98:2. However, in spite of the good yields of 9(11)-isomer the additional step constitutes a practical and an economical disadvantage.

The fact that prior investigators believed p-toluenesulfonic acid to be unsuitable to dehydrate 9-alpha-hydroxyandrostanes is perhaps the reason by German patent application DE No. 2814747 did not refer explicitly to the use of aromatic sulfonic acids. With non-aromatic, oxygen containing acids good results were obtained.

The present invention provides a method for the preparation of 9(11)-dehydro steroids in a high yield by dehydrating the corresponding 9-alpha-hydroxy steroids, giving a product in which only insignificant amounts of the undesired 8(9)-dehydro isomer are detectable.

It has surprisingly been found that 9-alpha-hydroxy steroids can be dehydrated in the presence of a Lewis acid, preferably in a solution. Preferred Lewis acids are; for example ferric chloride, boron trifluoride and its complexes such as the etherate, antimony pentachloride and titanium tetrachloride, but other Lewis acids such as aluminium chloride and tin chloride may be used as well. More preferably, a boron trifluoride complex is used, which is a cheap and readily available reagent. An extensive survey of Lewis acids can be found in Acta Chemica Scandinavica B40 (1986) 522–533. The acids may be used together with silicium dioxide.

The invention is applicable to steroids of the androstane and pregnane series having a common steroid structure illustrated by figures I and III, affording compounds of the type II and IV, respectively.

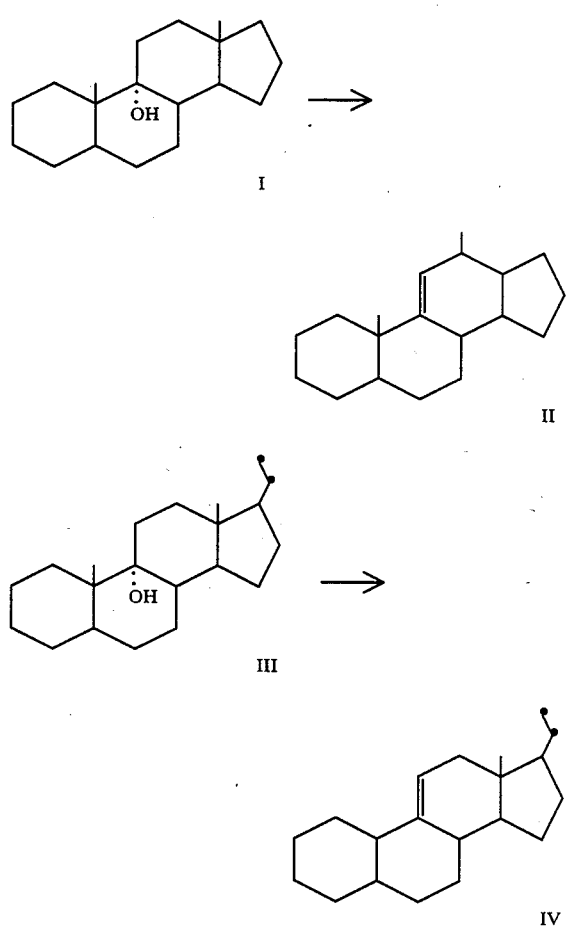

The invention is applicable whether the carbon atoms of the steroid nucleus and the pregnane side chain are substituted or not substituted and whether they are interconnected by double bonds or not. On carbon atom $C^{11}$ in structures I and III at least one hydrogen atom should be present to enable 9(11)-dehydration.

Any suitable inert organic solvent can be used but preferred solvents are benzene, toluene and methylene chloride, and, for $BF_3$ and its complexes, acetic acid or acetic anhydride. The reaction temperature varies between room temperature and reflux temperature. Depending on reaction conditions and the choice of catalyst the reaction time may vary from five minutes to three hours. Steroids which bear groups which are sensitive to a specific Lewis acid (e.g. 17-alpha-hydroxy, 20-ketopregnanes for a boron trifluoride complex) should be properly protected before dehydration.

A great advantage of the process according to the invention is that as previously mentioned the resulting 9(11)-dehydroandrostane contains little or no troublesome 8(9)-dehydroisomer. This isomer may be not distinguished from the 9(11)-isomer by thin layer chromatography because the $R_f$ values hardly differ. However, sensitive 360 MHz NMR-equipment can detect an amount as little as 0.5% of 8(9)-dehydro steroid using a difference of 12 Hz between (C(4)H-shifts of both isomers. For assessing the reaction yield a specific HPLC analysis may be developed, which is able to detect both isomers through their slightly different retention times. In the particular case of the dehydration of 9-alpha-hydroxyandrost-4-n-3,17-dione the relevant retention times are:

4.14 min: 9-alpha-hydroxyandrost-4-ene-3,17-dione
9.26 min: androsta-4,8-diene-3,17-dione
9.73 min: androsta-4,9(11)-diene-3,17-dione It should be understood that these retention times represent values resulting from a specifically developed HPLC system, characterized by a certain suitable mobile phase and a stationary phase. It will be appreciated that the removal of the 8(9)-dehydro byproduct is a difficult, hence costly operation. In the product prepared according to the invention there was no indication of the 8(9)-dehydro isomer when tested by NMR or HPLC-analysis.

An additional advantage is that the reaction is carried out in usual organic solvents, so that the dehydrated products without isolation can be further reacted in a multi-step process. Especially when anhydrous reaction conditions are desired this is a valuable feature (as proved in example 11).

Therefore the present invention provides a cheap and convenient method for the preparation of the important group of 9(11)-dehydro steroids in a high yield and at a high grade of purity.

The following examples illustrate the invention. NMR-spectra were recorded with 360 MHz proton NMR and with 20 MHz $C^{13}$ NMR. The NMR data were recorded in delta (ppm) units downfield from TMS. All percentages are by weight unless otherwise stated.

EXAMPLE 1

A suspension of 2.4 g of ferric chloride/silicium dioxide reagent (prepared according to A. Fadel and J. Salaün, Tetrahedron 41, 413 (1985)) and 0.40 g of 9-alpha-hydroxyandrost-4-ene-3,17-dione in 25 ml of anhydrous benzene was refluxed for 2 h. According to TLC (silica gel; toluene/acetone 3:1) the starting material was completely transformed into mainly androsta-4,9(11)-diene-3,17-dione. The reaction mixture was poured onto a chromatography column and eluted with acetone. The eluate was evaporated to dryness, the residue was dissolved in acetone, water was added and the acetone was removed by evaporation under reduced pressure. The resulting precipitate was filtered, washed with acetone/water (1:2) and dried.

The yield was 0.16 g of androsta-4,9(11)-diene-3,17-dione. According to NMR ($^{13}C$ and $^1H$) no 8(9)-dehydro isomer was present.

According to TLC the mother liquor still contained additional product.

NMR (CDCl$_3$): 0.891 ($C_{18}$-H$_3$), 1.369($C_{19}$-H$_3$), 5.56($C_{11}$-H), 5.75 ($C_4$-H).

EXAMPLE 2

A suspension of 0.2 g of anhydrous ferric chloride and 0.50 g of 9-alpha-hydroxyandrost-4-ene-3,17-dione in 25 ml of dry benzene was refluxed for 2 hrs. According to TLC (silica gel; toluene/acetone 3:1) the reaction was not complete, and the main product was androsta-4,9(11)-3,17-dione.

EXAMPLE 3

To a stirred solution of 604 mg of 9-alpha-hydroxyandrost-4-ene-3,17-dione in 20 ml of methylene chloride 1.28 ml of antimony pentachloride were added. The mixture was stirred at room temperature, for 1.5 h and next 20 ml of water were added to the dark coloured reaction mixture. It was stirred violently for 10 minutes, filtered and the water layer was removed.

The organic layer was washed with molar sodium bicarbonate solution and water (3x). The organic solution was then treated with charcoal and sodium sulphate, filtered and the filtrate was evaporated to dryness. The residue was crystallized from acetone to yield 139 mg of crude androsta-4,9(11)-diene-3,17-dione.

EXAMPLE 4

To a stirred suspension of 3.02 g of 9-alpha-hydroxyandrost-4-ene-3,17-dione in 150 ml of benzene 6.31 ml of boron trifluoride etherate were added. The mixture was refluxed for 0.5 h during which time a violet coloured solution was obtained. The mixture was then cooled to room temperature, 15 ml of water were added and the violet colour turned into yellow. The organic layer was separated and washed twice with 15 ml of water and, after the addition of methanol, evaporated to dryness. The crude product was crystallized successively from acetone and ethanol, yielding 2.3 g of pure androsta-4,9(11)-diene-3,17-dione; m.p. 204°-205.5° C.

NMR(CDCl$_3$): 0.891($C_{18}$-H$_3$), 1.371($C_{19}$-H$_3$), 5.57($C_{11}$-H) and 5.76 ($C_4$-H).

EXAMPLE 5

To a stirred suspension of 3.02 g of 9-alpha-hydroxyandrost-4-ene-3,17-dione (with a 97.5% purity) in 150 ml of dry benzene 5.48 ml of boron trifluoride methanol complex (50 mmol) were added. The reaction mixture was refluxed for 40 minutes. After cooling to room temperature 15 ml of water were added to the stirred reaction mixture. After 1 hour stirring the layers were separated. The organic phase was washed twice with water and evaporated under reduced pressure to afford 2.56 g of androsta-4,9(11)-diene-3,17-dione with a 89.5% purity and a 92.4% yield.

According to NMR ($^{13}C$ and $^1H$) and HPLC analysis no 8(9)-dehydro isomer was present.

EXAMPLE 6

To a stirred suspension of 3.02 g of 9-alpha-hydroxyandrost-4-ene 3,17-dione (with a 97.5% purity) in 150 ml of dry benzene 6.94 ml of boron trifluoride acetic acid complex were added. The reaction mixture was refluxed for 30 minutes. After cooling to room temperature 15 ml of water were added to the stirred reaction mixture. After stirring for 1 hour the layers were separated. The organic layer was washed twice with water and evaporated under reduced pressure to dryness to afford 2.83 g of androsta-4,9(11)-diene-3,17-dione with a 95.4% purity and a 97.5% yield. According to NMR ($^{13}C$ and $^{1}H$) and HPLC analysis no 8(9)-dehydro isomer was present.

EXAMPLE 7

To a stirred suspension of 3.02 g of 9-alpha-hydroxyandrost-4-ene-3,17-dione (with a 97.5% purity) in 150 ml of dry benzene 6.48 ml (50 mmol) of titanium tetrachloride were added. The reaction mixture was refluxed for 42 hours. After cooling to room temperature the mixture was washed three times with water and concentrated under reduced pressure to dryness. According to HPLC-analysis the crude product contained 0.40 g of androsta-4,9(11)-diene-3,17-dione (yield 14.4%). No 8(9)-dehydro isomer was detected.

EXAMPLE 8

To a stirred suspension of 3.16 g of 9-alpha-hydroxy-3-methoxyandrosta-3,5-dien-17-one in 150 ml of dry benzene 6.94 g of boron trifluoride acetic acid complex were added. The reaction mixture was stirred for 30 minutes. After cooling to room temperature the reaction mixture was stirred with 15 ml of water for 10 minutes. More water and ethyl acetate were added and the layers were separated. The organic layer was washed with water to neutral pH, dried and concentrated under reduced pressure to afford 2.73 g of androsta-4,9(11)-diene-3,17-dione with a 87% purity (HPLC).

EXAMPLE 9

To a stirred suspension of 0.40 g of 9-alpha,21-dihydroxypregna-4,16-diene-3,20-dione in 25 ml of dry benzene 2.4 g of anhydrous ferric chloride/silicium dioxide reagent (prepared according to Tetrahedron 41, 413 (1985) were added. The reaction mixture was refluxed for 45 minutes. After cooling to room temperature the reaction mixture was poured onto a short chromatography column (silica gel) and eluted with acetone. The eluate was concentrated under reduced pressure to dryness. The solid was dissolved in methylene chloride and water. The organic layer was washed twice with water, dried and concentrated under reduced pressure to afford 0.28 g of the crude product which was purified by chromatography (silica gel, toluene/acetone 5/1) to afford 21-hydroxypregna-4,9(11),16-triene-3,20-dione. No 8(9)-dehydro isomer was detected (NMR).

NMR (CDCl$_3$): 0.908 ($C^{18}H_3$), 1.371 ($C^{19}H_3$), 4.45, 4.54 ($C^{21}H_2$), 5.56 ($C^{11}H$), 5.75 ($C^4H$), 6.78 ($C^{16}H$).

EXAMPLE 10

To a stirred suspension of 5.75 g of 17-beta-cyano-9-alpha,17-alpha-dhydroxy-16-beta-methylandrost-4-en-3-one in 250 ml of benzene 11 ml of boron trifluoride etherate were added. The reaction mixture was stirred for 15 minutes. After cooling to room temperature ethyl acetate (200 ml) and water were added. The organic layer was separated, washed three times with water, filtered and concentrated under reduced pressure to dryness. The crude product was purified by crystallization from ethyl acetate to afford 3.39 g of 17-beta-cyano-17-alpha-hydroxy-16-beta-methylandrosta-4,9(11)-dien-3-one.

M.p. 189°–191° C. (dec.)

NMR (CDCl$_3$): 0.929 ($C^{18}H_3$), 1.31 ($C^{16}CH_3$), 1.347 ($C^{19}H_3$), 5.58 ($C^{11}H$), 5.75 ($C^4H$).

EXAMPLE 11

To a stirred suspension of 6.58 g (20 mmol) of 17-beta-cyano-9-alpha,17-alpha-dihydroxyandrost-4-en-3-one in 300 ml of benzene 12.6 ml (100 mmol) of boron trifluoride etherate were added. After refluxing for 20 minutes the reaction mixture was cooled to room temperature. Methanol (30 ml) was added to the reaction mixture and next a clear solution was formed. The reaction mixture was cooled in an ice bath and saturated with hydrogen chloride gas and stirred in a sealed bottle at room temperature for 17 hours. After cooling in an ice bath ice (150 g) was added to the reaction mixture. The organic layer was separated and washed three times with water. The combined aqueous layers (500 ml) were stirred at room temperature for 20 hours during which product crystallized. The crystals were filtered, washed with water and dried. The crude product (5.14 g) was purified over silica gel with diethyl ether. Crystallization from diethyl ether afforded 3.81 g (55%) of pure methyl 17-alpha-hydroxy-3-oxoandrosta-4,9(11)-dien-17-alpha-carboxylate. According to NMR ($^{13}C$ and $^{1}H$) no 8(9)-dehydro isomer was present.

M.p. 199.5°–197° C.

NMR (CDCl$_3$): 0.679 ($C^{18}H_3$), 1.343 ($C^{19}H_3$), 3.00 (17-OH), 3.78 (COOCH$_3$), 5.55 ($C^{11}H$), 5.74 ($C^4H$).

We claim:

1. Process for preparing a 9(11)-dehydro steroid selected from the group consisting of androstane and pregnane series steroids, comprising
   providing a 9-alpha-hydroxy steroid selected from the group consisting of androstane and pregnane series steroids, said 9-alpha-hydroxy steroid having at least one hydrogen atom at the C-11 position; and
   dehydrating said 9-alpha-hydroxy steroid in an inert organic solvent in the presence of a Lewis acid thereby removing the 9-alpha-hydroxy group and the hydroxy atom at the C-11 position and producing the corresponding 9(11)-dehydro steroid.

2. Process according to claim 1, characterized in that the Lewis acid is selected from the group consisting of ferric chloride, boron trifluoride, boron trifluoride complexes, antimony pentachloride, titanium tetrachloride and mixtures of these compounds with silicium dioxide.

3. Process according to claim 1, characterized in that the Lewis acid is a boron trifluoride complex.

4. Process according to claim 1 characterized in that the process is carried out at a temperature between room temperature and reflux temperature.

5. Process according to claim 1, further comprising the step of protecting Lewis-acid-sensitive groups on said 9-alpha-hydroxy steroid other than the 9-alpha-hydroxy group prior to dehydrating said 9-alpha-hydroxy steroid.

* * * * *

UNITED STATES PATENT AND TRADEMARK OFFICE
CERTIFICATE OF CORRECTION

PATENT NO. : 4,917,827

DATED : April 17, 1990

INVENTOR(S) : Jacobus N. M. BATIST et al.

It is certified that error appears in the above-identified patent and that said Letters Patent is hereby corrected as shown below:

Col. 2, lines 26-32, compound II should be shown as follows:

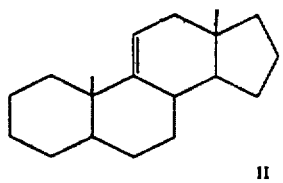

II

Col. 2, lines 45-52, compound IV should be shown as follows:

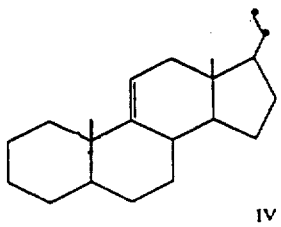

IV

Col. 3, line 17, cancel "4-n-3", insert --4-ene-3--.

Col. 4, line 53, cancel "2.56", insert --2.86--.

Col. 5, line 53, cancel "dhydroxy", insert --dihydroxy--.

Col. 6, line 27, cancel "alpha", insert --beta--.

Col. 6, line 29, cancel "199.5", insert --195.5--.

UNITED STATES PATENT AND TRADEMARK OFFICE
CERTIFICATE OF CORRECTION

PATENT NO. : 4,917,827

DATED : April 17, 1990

INVENTOR(S) : Jacobus N. M. Batist, et al.

It is certified that error appears in the above-identified patent and that said Letters Patent is hereby corrected as shown below:

Col. 6, line 44, cancel "hydroxy", insert --hydrogen--.

Signed and Sealed this

Twelfth Day of November, 1991

Attest:

HARRY F. MANBECK, JR.

*Attesting Officer*     *Commissioner of Patents and Trademarks*